Figure 4:
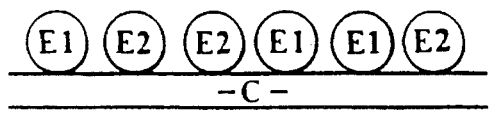
Figure 4:
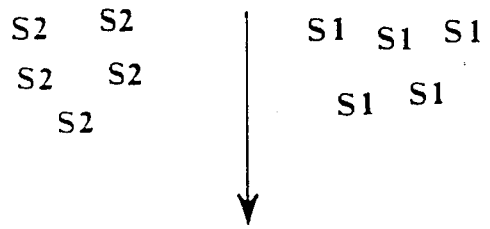
Figure 4:
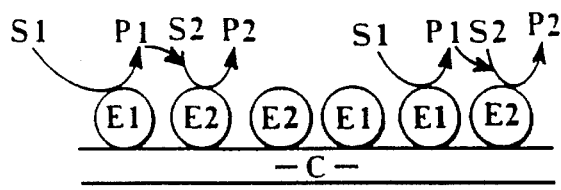

United States Patent [19]

Pollard-Knight

[11] Patent Number: 5,496,701
[45] Date of Patent: Mar. 5, 1996

[54] OPTICAL BIOSENSOR METHOD FOR DETERMINING AN ANALYTE

[75] Inventor: Denise V. Pollard-Knight, St. Albans, Great Britain

[73] Assignee: Fisons plc, United Kingdom

[21] Appl. No.: 157,079

[22] PCT Filed: Jun. 2, 1992

[86] PCT No.: PCT/GB92/00991

§ 371 Date: Dec. 3, 1993

§ 102(e) Date: Dec. 3, 1993

[87] PCT Pub. No.: WO92/21768

PCT Pub. Date: Dec. 10, 1992

[30] Foreign Application Priority Data

Jun. 4, 1991 [GB] United Kingdom .................. 9111912

[51] Int. Cl.[6] .................................................. G01N 33/573
[52] U.S. Cl. ........................... 435/7.4; 385/129; 385/130; 385/131; 422/82.05; 422/82.11; 435/7.91; 435/176; 435/808; 436/164; 436/518; 436/527; 436/805
[58] Field of Search ...................... 385/129–131; 422/82.05, 82.06, 82.09, 82.11, 57, 55; 435/7.4, 7.91, 176, 808; 436/518, 527, 164, 805; 356/318

[56] References Cited

U.S. PATENT DOCUMENTS

| 4,857,273 | 8/1989 | Stewart | 422/55 |
| 4,992,385 | 2/1991 | Godfrey | 422/82.11 |

FOREIGN PATENT DOCUMENTS

| WO-A-9006503 | 6/1990 | WIPO . |
| WO-A-9011510 | 10/1990 | WIPO . |

OTHER PUBLICATIONS

Schaap et al., "Chemiluminescent Substrates for Alkaline Phosphatase: Application to Ultrasensitive Enzyme–Linked Immunoassays and DNA Probes", Clinical Chemistry, vol. 35, No. 9, 1989, pp. 1863–1864.

*Primary Examiner*—David Saunders
*Assistant Examiner*—Christopher L. Chi
*Attorney, Agent, or Firm*—Nixon, Hargrave, Devans & Doyle

[57] ABSTRACT

A method for determining one member of an enzyme-substrate pair (the analyte), comprises bringing the members of the pair into contact so as to form, directly or indirectly, a soluble reaction product at or adjacent the surface of an optical waveguide biosensor. The biosensor is preferably a resonant optical biosensor based on the principle of frustrated total reflection.

11 Claims, 2 Drawing Sheets

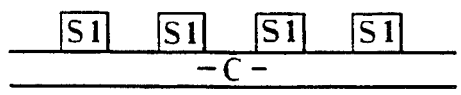
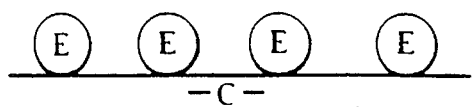
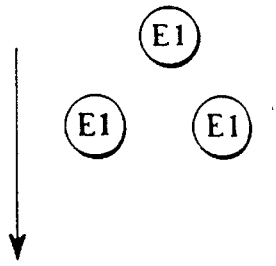
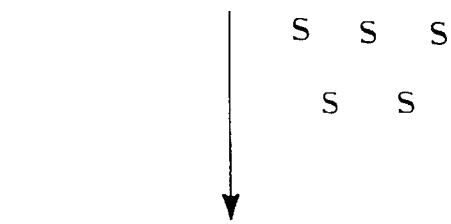
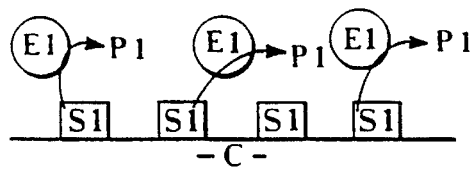
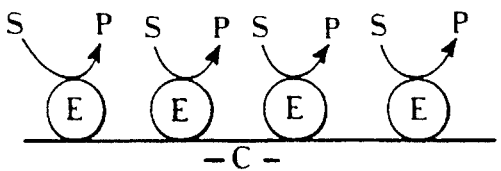
FIG 1            FIG 2
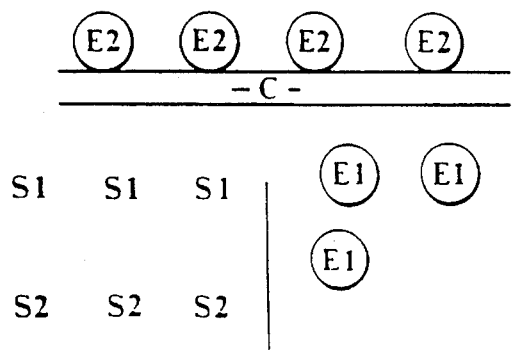
FIG 3
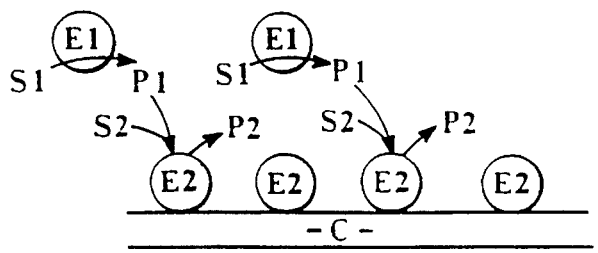

OPTICAL BIOSENSOR METHOD FOR DETERMINING AN ANALYTE

This invention relates to methods for the qualitative or quantitative determination of biomolecules in solution, in particular to methods for the determination of enzymes and their substrates in samples of biological origin.

Many devices for the automatic determination of biochemical analytes in solution have been proposed in recent years. Typically, such devices (biosensors) include a sensitised coating layer which is located in the evanescent region of a resonant field. Detection of the analyte typically utilizes optical techniques such as, for example, surface plasmon resonance (SPR), and is based on changes in the thickness and/or refractive index of the coating layer resulting from interaction of that layer with the analyte. This causes a change, e.g. in the angular position of the resonance.

Other optical biosensors include a waveguide in which a beam of light is propagated. The optical characteristics of the device are influenced by changes occurring at the surface of the waveguide. One form of optical biosensor is based on frustrated total reflection. The principles of frustrated total reflection (FTR) are well-known; the technique is described, for example, by Bosacchi and Oehrle [Applied Optics (1982), 21, 2167–2173]. An FTR device for use in immunoassay is disclosed in U.S. Pat. No. 4,857,273 and comprises a cavity layer bounded on one side by the sample under investigation and on the other side by a spacer layer which in turn is mounted on a substrate. The substrate-spacer layer interface is irradiated with monochromatic radiation such that total reflection occurs, the associated evanescent field penetrating through the spacer layer. If the thickness of the spacer layer is correct and the incident parallel wave vector matches one of the resonant mode propagation constants, the total reflection is frustrated and radiation is coupled into the cavity layer. The cavity layer must be composed of material which has a higher refractive index than the spacer layer and which is transparent at the wavelength of the incident radiation.

More recently, FTR biosensors have been described [see, for example, PCT Patent Application WO 90/06503] in which the cavity layer is a thin film of relatively high refractive index material, typically an inorganic oxide.

In all biosensors, it is necessary that the sensitised coating layer comprise a layer of immobilised chemical or biochemical species. Methods have been disclosed [see PCT Patent Application No WO 90/11510] for the determination of one member of an enzyme-substrate pair which comprise immobilising the other member of that pair on the surface of an SPR biosensor and monitoring the effect of deposition of the reaction product on the surface of the device. Obviously, to have an effect on the characteristics of the device, the reaction product must be insoluble and this places great constraints on the range of enzymes and substrates which may be determined by this method. Also, the deposition of the insoluble product on the surface means that the device is generally not re-usable.

We have now devised methods of determining enzymes and their substrates using a biosensor which overcome or substantially mitigate these disadvantages.

According to the invention, there is provided a method of determining one member of an enzyme-substrate pair (the analyte), which comprises bringing the members of the pair into contact so as to form, directly or indirectly, an absorbing reaction product at or in the vicinity of the surface of an optical waveguide biosensor.

The method of the invention is advantageous in that enzymes and substrates which produce soluble, absorbing reaction products are more widely available than those which produce insoluble products. This means that the number of enzymes and substrates which can be directly assayed is significantly greater. In many cases appropriate substrates can be easily synthesised de novo, which is not the case for substrates which result in insoluble products. Also, if it is the enzyme which is immobilised on the sensor surface, and if the enzymes maintain their activity, the sensor can be re-used for several samples. Again, this is not the case for insoluble reaction products.

Any convenient parameter of the emitted radiation may be monitored. Obviously, the absorbing nature of the reaction product will have an effect on the intensity of the radiation coupled out of the waveguide. The product may also be fluorescent or luminescent and it may be the fluorescence or luminescence which is monitored.

One specific embodiment of the method according to the invention comprises the steps of a) contacting a sample, in which the analyte is to be determined, with the surface of an optical waveguide biosensor on which the other member of the enzyme-substrate pair is immobilised, so as to form (if the analyte is present) a soluble, absorbing reaction product, b) irradiating the biosensor with a beam of electromagnetic radiation such that propagation of light of a wavelength absorbed by the reaction product occurs within the waveguide, and c) monitoring the radiation emitted from the biosensor.

The method of the invention may also be used to determine analytes which influence the rate of the enzyme-substrate reaction, ie enzyme inhibitors and activators. In this case, the method may comprise a) contacting a sample, in which an inhibitor or activator of an enzyme is to be determined, with the surface of an optical waveguide biosensor on which an enzyme or a substrate therefor is immobilised, the substrate being one which in the presence of the enzyme produces a soluble, absorbing reaction product, b) adding to the sample the other member of the enzyme-substrate pair, c) irradiating the biosensor with a beam of electromagnetic radiation such that propagation of light of a wavelength absorbed by the reaction product occurs within the waveguide, and d) monitoring the radiation emitted from the biosensor.

In this method, the formation of absorbing reaction product correlates with the concentration of activator in the sample, or correlates inversely with the concentration of inhibitor.

In a variation on the method of the invention, where the analyte is the substrate which does not produce an absorbing reaction product, a substrate analogue which does do so may be added to the sample before contacting it with the sensor surface. The substrate analogue then competes with the natural substrate for binding to the immobilised enzyme.

In another variation, the invention also provides a method for determining one member of an enzyme-substrate pair (the analyte), which comprises a) contacting a sample, in which the analyte is to be determined, with the surface of an optical waveguide biosensor on which a second enzyme is immobilised, b) adding to the sample the other member of the enzyme-substrate pair and a substrate for the immobilised enzyme which, in the presence of a reaction product of the enzyme-substrate pair, produces a soluble, absorbing reaction product, c) irradiating the biosensor with a beam of electromagnetic radiation such that propagation of light of a wavelength absorbed by the reaction product occurs within the waveguide, and d) monitoring the radiation emitted from the biosensor.

Where the analyte is the substrate, both enzymes may be immobilised on the sensor surface. One enzyme reacts with the substrate in the sample to produce a product which in the presence of the substrate for the second enzyme reacts to form the absorbing, soluble reaction product.

The soluble reaction products must not diffuse out of the evanescent field of the optical waveguide sensor during the course of the assay, but must remain localised close to the immobilised enzyme. This is known to occur for some enzymes. For example, in the assay of alkaline phosphatase using the substrate dioxetane phosphate in the presence of a detergent-solubilised derivative of fluorescein [Schaap et al (1989) Clin Chem 35, 1863–1864], the luminescent signal produced remains localised close to the enzyme active site. For those enzymes for which this is not the case the reaction product may be kept within the evanescent field by means of a physical barrier or by capture on the sensor surface by means of an antibody. For example, antibodies may be prepared which bind the product of the enzyme reaction but not the substrate. The antibodies may be immobilised on the same chip as the enzymes.

If the reaction products are constrained to the vicinity of the surface at which they are formed, it may be possible to detect several analytes within the same sample.

Examples of some suitable enzyme-substrate pairs are the following:

| Absorbing product | |
|---|---|
| β-galactosidase | resorufin-β-D-galactopyranoside |
| β-galactosidase | methoxy-1-naphthyl-β-D-galactopyranoside |
| B-glucuronidase | resorufin-β-D-glucuronide |
| Fluorescent product | |
| siayltransferases | cytidine-5-monophosphate-(3-fluoresceinyl-thioureido)-deoxy-N-acetyl-neuramic acid |
| β-galactosidase | fluorescein di-(β-D-galactopyranoside) |
| Luminescent product | |
| alkaline phosphatase | dioxetane phosphate in the presence of a detergent-solubilised derivative fluorescein |
| firefly luciferase | ATP and luciferin |

Assays for some enzymes may be performed by observing a decrease in the absorbance at a particular wavelength. For example, angiotensin converting enzyme may be assayed with the substrate FA-Phe-Gly-Gly (FA is furylacryloyl) by observing a decrease in absorbance.

Enzymes for which there are no suitable substrates for direct measurement may be detected by the use of a coupling enzyme. For example, oxalate oxidase may be detected as follows:

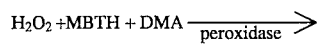

MBTH = 3-methyl-2-benzothiazolinone hydrazone
DMA = N,N-dimethylaniline

Alternatively, a suitable, simple chemical reaction which uses the reaction product to produce an absorbing species may be available. For example, creatine kinase or phosphocreatine may be assayed as follows:

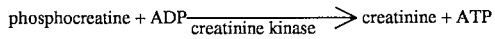

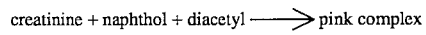

The methods according to the invention may be conducted with any form of optical waveguide biosensor. However, it is preferred to use a resonant biosensor based on the principle of frustrated total reflection (FTR). Such a biosensor typically comprises a) a cavity layer of dielectric material of refractive index $n_3$, b) a dielectric substrate of refractive index $n_1$, and c) interposed between the cavity layer and the substrate, a dielectric spacer layer of refractive index $n_2$.

In use, the interface between the substrate and the spacer layer is irradiated with light such that total reflection occurs. In this context, 'light' may include not only visible light but also wavelengths above and below this range, e.g. in the ultra-violet and infra-red.

Resonant propagation of a guided mode in the cavity layer will occur, for a given wavelength, at a particular angle of incidence of the exciting radiation. Thus, two basic measurement approaches are possible: scanning the angle of incidence at fixed wavelength or scanning the wavelength at a fixed angle of incidence. The former approach, using monochromatic radiation, is preferred since it allows the use of a laser source, simplifying the problem of optical collimation, and avoids dispersion effects, thereby simplifying the analysis of the results.

The angular position of the resonant effect depends on various parameters of the biosensor device, such as the refractive indices and thicknesses of the various layers. In general, it is a pre-requisite that the refractive index $n_3$ of the cavity layer and the refractive index $n_1$ of the substrate should both exceed the refractive index $n_2$ of the spacer layer. Also, since at least one mode must exist in the cavity to achieve resonance, the cavity layer must exceed a certain minimum thickness.

The cavity layer is preferably a thin-film of dielectric material. Suitably transmissive dielectric materials for the cavity layer include zirconium dioxide, titanium dioxide, aluminium oxide and tantalum oxide.

The cavity layer may be prepared by known techniques, e.g. vacuum evaporation, sputtering, chemical vapour deposition or in-diffusion.

The dielectric spacer layer must also be suitably transmissive to the incident radiation and must have a lower refractive index than both the cavity layer and the substrate. The layer may, for example, comprise an evaporated or sputtered layer of magnesium fluoride. In this case an infra-red light injection laser may be used as light source. The light from such a source typically has a wavelength around 800 nm. Other suitable materials include lithium fluoride and silicon dioxide. Apart from the evaporation and sputtering techniques mentioned above, the spacer layer may be deposited on the substrate by a sol-gel process, or be formed by chemical reaction with the substrate.

The refractive index of the substrate ($n_1$) must be greater than that ($n_2$) of the spacer layer but the thickness of the substrate is generally not critical to the performance of the invention.

By contrast, the thickness of the cavity layer must be so chosen that resonance occurs within an appropriate range of coupling angles. The spacer layer will typically have a thickness of the order of several hundred nanometers, say from about 200 nm to 2000 nm, more preferably 500 to 1500 nm, e.g. 1000 nm. The cavity layer typically has a thickness of a few tens of nanometers, say 10 to 200 nm, more preferably 30 to 150 nm, e.g. 100 nm.

It is particularly preferred that the cavity layer has a thickness of 30 to 150 nm and comprises a material selected from zirconium dioxide, hafnia, silicon nitride, titanium dioxide, tantalum oxide and aluminium oxide, and the spacer layer has a thickness of 500 to 1500 nm and comprises a material selected from magnesium fluoride, lithium fluoride and silicon dioxide, the choice of materials being such that the refractive index of the spacer layer is less than that of the cavity layer.

Preferred materials for the cavity layer and the spacer layer are tantalum oxide and silicon dioxide respectively.

Any convenient source of radiation may be used as the source of the incident light but it is preferable to use monochromatic radiation and the most convenient source of such radiation is a laser. The choice of laser will depend inter alia on the materials used for the various layers of which some examples have already been given, and of course on the particular absorbing reaction product.

The scanning of angle may be performed either sequentially ie by varying the angle of incidence of a parallel beam of light or by simultaneously irradiating over a range of angles using a fan-shaped beam of light as described (in connection with SPR) in European Patent Application No 0305109A. In the former case, a single-channel detector may be used which is mechanically scanned over a range of angles; in the latter case, in which a range of angles is irradiated simultaneously, it will generally be necessary to use a multi-channel detector having angular resolution.

At resonance, the incident light is coupled into the cavity layer by FTR, propagates a certain distance along the cavity layer, and couples back out (also by FTR). The propagation distance depends on the various device parameters but is typically of the order of 1 or 2 mm.

The formation of absorbing reaction product in the course of the methods according to the invention may result in a reduction in the intensity of the reflected light. If the reaction product is fluorescent or luminescent, the increase in intensity at the fluorescent or luminescent wavelengths may be used to determine the analyte.

Some methods according to the invention will now be illustrated further with reference to the accompanying Figures.

FIG. 1 shows schematically an assay method for the determination of an enzyme E1. A substrate S1 for the enzyme is immobilised on the surface of the cavity layer C of an FTR biosensor. The substrate S1 may be immobilised directly on the layer C or may be immobilised in a layer of gel. When a sample containing the enzyme E1 is brought into contact with the biosensor surface C, a detectable (absorbing) product P1 is produced.

FIG. 2 shows a corresponding method for the determination of a substrate S. In this case, it is the enzyme E which is immobilised on the sensor surface C.

In the scheme shown in FIG. 3 for the determination of an enzyme E1, a coupling enzyme E2 is immobilised on the surface C. To the sample containing E1 is added a substrate S1 for that enzyme and a substrate S2 for the coupling enzyme E2 which in the presence of the product P1 (produced from S1 by the action of E1) produces a detectable (absorbing) product P2.

FIG. 4 shows a scheme in which the substrate S1 is the analyte and two enzymes E1 and E2 are immobilised on the sensor C. A coupling substrate S2 is added to the sample containing S1. The analyte substrate S1 is converted by enzyme E1 to a product P1 which reacts, in the presence of enzyme E2, with the coupling substrate S2 to produce a detectable (absorbing product) P2.

Figure 5:
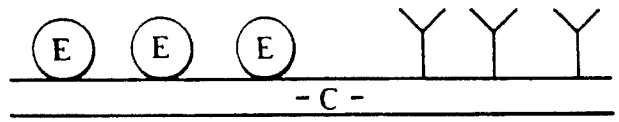
Figure 5:
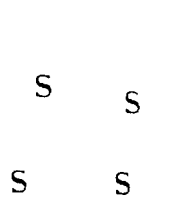
Figure 5:
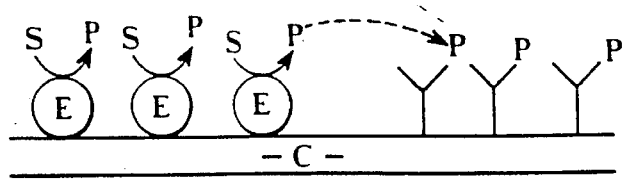

FIG. 5 shows a variation on the scheme shown in FIG. 2 in which the reaction product P is captured and retained at the surface C of the sensor by immobilised specific antibodies.

What is claimed is:

1. A method of determining an analyte, wherein said analyte is one of two members of an enzyme-substrate pair, comprising:

immobilizing a first member of said enzyme-substrate pair on a surface of an optical waveguide biosensor, bringing a second member of said pair into contact with said first member at said surface of said optical waveguide biosensor, wherein the members of said pair are selected to form, directly or indirectly, a soluble reaction product, irradiating the biosensor with radiation from a radiation source, said radiation being of a wavelength at which the reaction product is absorbing, whereby radiation is emitted from the biosensor, monitoring the radiation emitted, and correlating the radiation emitted to the presence of the analyte.

2. A method as claimed in claim 1, wherein said bringing is carried out by contacting a sample, in which said analyte is to be determined, with the surface of an optical waveguide biosensor, and said irradiating is carried out with a beam of electromagnetic radiation such that propagation of light of a wavelength absorbed by the reaction product occurs within the biosensor.

3. A method as claimed in claim 1, further comprising constraining the reaction product on the surface of the biosensor by capturing the reaction product on the surface of the biosensor with a binding material capable of binding said reaction product, wherein said binding material is immobilized on the surface of the biosensor.

4. A method as claimed in claim 1, wherein the optical waveguide biosensor is a resonant biosensor based on the principle of frustrated total reflection, said biosensor comprising;

a cavity layer of dielectric material of refractive index $n_3$, a dielectric substrate of refractive index $n_1$, and interposed between the cavity layer and the substrate, a dielectric spacer layer of refractive index $n_2$.

5. A method as claimed in claim 4, wherein the cavity layer is thin-film of dielectric material.

6. A method as claimed in claim 4, wherein the cavity layer has a thickness of 30 to 150 nm and comprises a material selected from the group consisting of zirconium dioxide, hafnia, silicon nitride, titanium dioxide, tantalum oxide and aluminum oxide, and the spacer layer has a thickness of 500 to 1500 nm and comprises a material selected from the group consisting of magnesium fluoride, lithium fluoride and silicon dioxide, wherein the refractive index of the spacer layer is less than that of the cavity layer.

7. A method as claimed in claim 1, further comprising constraining the reaction product in the region adjacent the surface of the biosensor with a physical barrier.

8. A method for the determination of an analyte which influences the rate of a reaction between an enzyme and a substrate, which method comprises:

contacting a sample containing said analyte with a surface of an optical waveguide biosensor on which said enzyme or said substrate is immobilized, wherein said enzyme and said substrate are selected to form a soluble reaction product, adding to the sample the other member of the enzyme-substrate pair, irradiating the biosensor with a beam of electromagnetic radiation such that propagation of light of a wavelength absorbed by the reaction product occurs within the biosensor, and radiation is emitted from the biosensor, monitoring the radiation emitted, and correlating the radiation emitted to the presence of the analyte.

9. A method for determining an analyte in a sample, wherein said analyte is a substrate capable of reacting with an enzyme to form a reaction product which does not absorb electromagnetic radiation of a particular wavelength, said method comprising:

immobilizing said enzyme on a surface of an optical waveguide biosensor, adding a substrate analogue to the sample, wherein said substrate analogue is selected to react with said enzyme to form, directly or indirectly, a soluble reaction product which absorbs at said particular wavelength, contacting the sample after said adding with said surface of said optical waveguide biosensor, irradiating the biosensor with radiation of said particular wavelength from a radiation source, whereby radiation is emitted from the biosensor, monitoring the radiation emitted, and correlating the radiation emitted to the presence of the analyte.

10. A method of determining an analyte, wherein the analyte is one of two members of a first enzyme-first substrate pair, comprising:

contacting a sample, in which the analyte is to be determined, with a surface of an optical waveguide biosensor on which a second enzyme is immobilized, adding to the sample the other member of the first enzyme-first substrate pair, and a second substrate which reacts with said second enzyme in the presence of a reaction product of the first enzyme-first substrate pair to produce a soluble reaction product, irradiating the biosensor with a beam of electromagnetic radiation such that propagation of light of a wavelength absorbed by said soluble reaction product occurs within the biosensor, and radiation is emitted from the biosensor, monitoring the radiation emitted, and correlating the radiation emitted to the presence of the analyte.

11. A method as claimed in claim 10, wherein said first enzyme and said second enzyme are immobilized on the surface of the biosensor.

* * * * *